(12) United States Patent
Shiraki

(10) Patent No.: US 12,201,447 B2
(45) Date of Patent: Jan. 21, 2025

(54) SENSOR DEVICE, NOTIFICATION METHOD, POUCH, AND NOTIFICATION SYSTEM

(71) Applicant: SINTOKOGIO, LTD., Nagoya (JP)

(72) Inventor: Masataka Shiraki, Nagoya (JP)

(73) Assignee: SINTOKOGIO, LTD., Aichi (JP)

( * ) Notice: Subject to any disclaimer, the term of this patent is extended or adjusted under 35 U.S.C. 154(b) by 0 days.

(21) Appl. No.: 17/883,964

(22) Filed: Aug. 9, 2022

(65) Prior Publication Data

US 2023/0050302 A1 Feb. 16, 2023

(30) Foreign Application Priority Data

Aug. 10, 2021 (JP) .................. 2021-130895

(51) Int. Cl.
*A61B 5/00* (2006.01)
*A61F 5/449* (2006.01)
*G01N 33/00* (2006.01)

(52) U.S. Cl.
CPC ............ *A61B 5/6802* (2013.01); *A61B 5/742* (2013.01); *A61F 5/449* (2013.01); *G01N 33/0031* (2013.01)

(58) Field of Classification Search
CPC ........ A61F 5/445; A61F 5/449; A61F 5/4404; A61B 5/339; A61B 5/68; A61B 5/6801; A61B 5/6802; A61B 5/6811; A61B 5/742; G01N 33/0031
See application file for complete search history.

(56) References Cited

U.S. PATENT DOCUMENTS

| 9,928,341 | B2 | 3/2018 | Angelides |
| 2016/0270697 | A1* | 9/2016 | Hatakeyama .......... A61B 5/113 |
| 2017/0045797 | A1 | 2/2017 | Yamamoto et al. |
| 2017/0140103 | A1* | 5/2017 | Angelides ............. A61F 5/4404 |
| 2020/0188161 | A1* | 6/2020 | Seres ..................... G01K 13/00 |
| 2021/0100533 | A1 | 4/2021 | Seres et al. |
| 2021/0361465 | A1* | 11/2021 | Hansen .................. A61F 5/445 |
| 2022/0226143 | A1* | 7/2022 | Negrete .................. A61F 5/449 |

FOREIGN PATENT DOCUMENTS

| EP | 0661027 A1 | 7/1995 |
| JP | H04-102460 A | 4/1992 |
| JP | 2020039496 A1 | 3/2021 |

OTHER PUBLICATIONS

European Search Report dated Dec. 1, 2022.
EP Office Action for corresponding European Patent Application No. 22189227.6 dated Oct. 19, 2023.
JP Office Action for Japanese Patent Application No. 2021-130895 issued on Nov. 5, 2024, and English machine translation thereof.

* cited by examiner

*Primary Examiner* — Ariana Zimbouski
*Assistant Examiner* — Timothy L Flynn
(74) *Attorney, Agent, or Firm* — Harness, Dickey & Pierce, P.L.C.

(57) ABSTRACT

Provided is a sensor device capable of detecting leakage from a pouch with a higher accuracy. An odor sensor (41) detects odor leaking from a pouch (3) attached to a stoma (21) of a user (2). A radio communication interface (42) notifies, via a notification device (5), the user (2) that odor is detected.

6 Claims, 7 Drawing Sheets

SENSOR DEVICE, NOTIFICATION METHOD, POUCH, AND NOTIFICATION SYSTEM

This Nonprovisional application claims priority under 35 U.S.C. § 119 on Patent Application No. 2021-130895 filed in Japan on Aug. 10, 2021, the entire contents of which are hereby incorporated by reference.

TECHNICAL FIELD

The present invention relates to a sensor device, a notification method, a pouch, and a notification system.

BACKGROUND ART

For ostomates who use a pouch on an ordinary basis, leakage from the pouch is one of major concerns. While constantly wearing the pouches attached to them, the ostomates perform daily activities as people around them do. Thus, many ostomates strongly desire not to trouble the people around them due to leakage of odor of stool and/or a gaseous matter (flatus) from the pouch.

Conventional pouches are designed in various ways to prevent odor leakage. For example, in order to minimize odor leakage as much as possible, some pouches are designed to include a face plate having an adhesive for making the face plate strongly adhere to a skin and/or to include a deodorant in the pouch. Still, there is no guarantee to completely prevent odor leakage. Due to lack of such a guarantee, many ostomates have no choice but to use the pouch while worrying about the possibility of occurrence of odor leakage.

In such circumstances, as a conventional technique, Patent Literature 1 proposes a technique of detecting leakage of excreta stored in a pouch and giving a warning to a user. Patent Literature 1 discloses a method for detecting an internal pressure of a pouch by measuring, with use of a pneumatic electronic converter that converts an air pressure into an electric signal, an air pressure in a small chamber that has an opening and that is coupled to a surrounding area of a hole formed in the pouch. Patent Literature 1 further discloses a warning device that employs this method.

CITATION LIST

Patent Literature

Patent Literature 1
Japanese Patent Application, Tokugan, No. 2020-537923

SUMMARY OF INVENTION

Technical Problem

According to the above-described technique, however, unless the pressure in the pouch rises sufficiently, it is impossible to detect the pressure rise. Thus, if odor (gaseous matter=flatus) leaks from a gap between the face plate and the skin when the pressure rise is not sufficient, it is impossible to detect the pressure rise, thereby leading to a failure to detect the leakage. As discussed above, the conventional technique has a disadvantage of low accuracy in detection of leakage from a pouch.

An aspect of the present invention was made in view of the above-described problem, and has an object to provide a sensor device capable of detecting leakage from a pouch with a higher accuracy.

Solution to Problem

In order to attain the above-described object, a sensor device in accordance with an aspect of the present invention includes: an odor sensor that detects odor leaking from a pouch attached to a stoma of a user; and a notification section that notifies the user that the odor is detected.

Advantageous Effects of Invention

In accordance with an aspect of the present invention, it is possible to provide a sensor device capable of detecting leakage from a pouch with a higher accuracy.

DESCRIPTION OF EMBODIMENTS (Configuration of Notification System 1)

Figure 1:
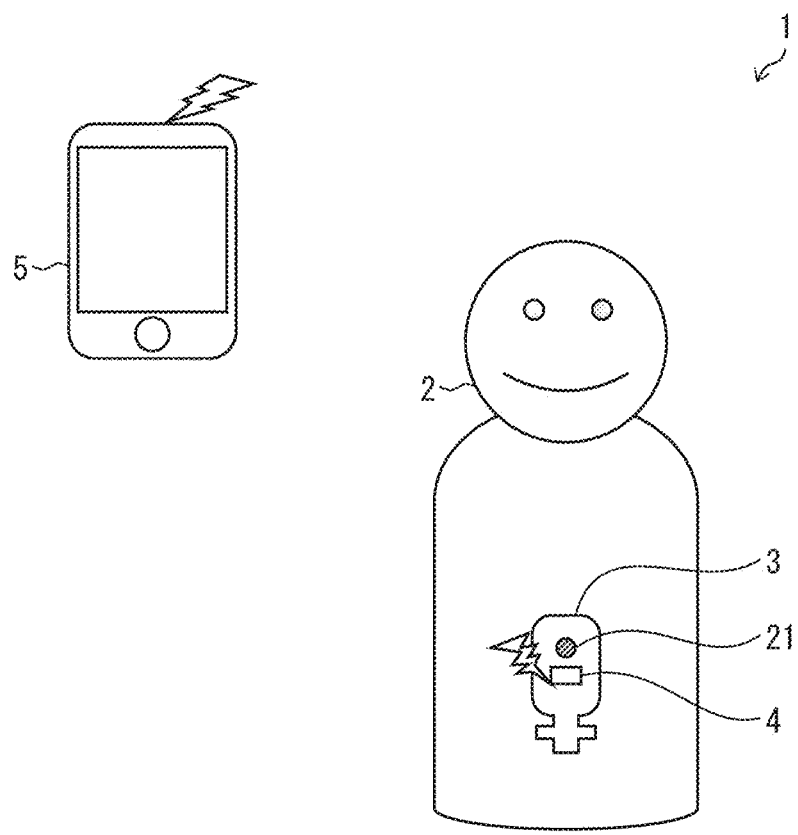
FIG. 1 is a view illustrating a configuration of a notification system in accordance with an embodiment of the present invention.

FIG. 1 is a view illustrating a configuration of a notification system 1 in accordance with an embodiment of the present invention. In the present embodiment, a user 2 who is an ostomate uses the notification system 1. The user 2 has a stoma 21 (artificial anus) on his/her abdominal region. The user 2, who has lost his/her anus, should use the stoma 21 to empty his/her bowels. Unlike the anus, the stoma 21 does not have sphincter muscle. Thus, the user 2 cannot control the stoma 21 with his/her own will to empty his/her bowels or to hold it. In order to address this, the user 2 uses a pouch 3 attached to the stoma 21 to receive, by the pouch 3, stool that is discharged from the stoma 21 regardless of user's will. The pouch 3 may also be called a stoma prosthesis.

Provided that the pouch 3 is attached to the user 2 correctly, stool and/or a gaseous matter (flatus) discharged from the stoma 21 can be appropriately received by a storage bag 31 of the pouch 3. Thus, the stool and/or gaseous matter discharged from the stoma 21 would not leak outside the pouch 3. However, in a case where the user 2 is still unused to attachment of the pouch 3, the user 2 may possibly finish attachment of the pouch 3 in a state where a gap is left between the pouch 3 and a skin of the user 2. In another case, even if the user 2 can attach the pouch 3 correctly, a gap may possibly be generated between the pouch 3 and the skin of the user 2 due to a motion and/or sweat of the user 2 after a lapse of a long period of time since the attachment. In either case, odor inside the pouch 3 would leak through the gap, which may give a stress on the user 2. Furthermore, the user 2 is forced to be anxious about the possibility of occurrence of odor leakage from the pouch 3. Thus, the user 2 must perform daily activities while worrying about odor leakage. This can be a mental burden on the user 2.

In order to deal with this, the user 2 can use the notification system 1 in accordance with the present embodiment to perform daily activities at ease while wearing the pouch 3 attached to him/her. As shown in FIG. 1, the notification system 1 includes a sensor device 4 and a notification device 5. The sensor device 4 is a device that detects odor leakage from the pouch 3. The notification device 5 notifies the user 2 of odor leakage if the odor leakage from the pouch 3 is detected by the sensor device 4. The details of functions and operation of the sensor device 4 and the notification device 5 will be described later.

(Configuration of Stoma 21)

Figure 2:
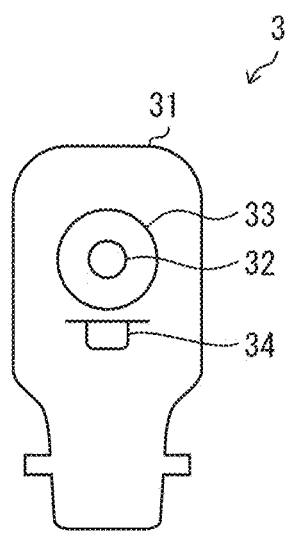
FIG. 2 is a view illustrating a configuration of a pouch in accordance with an embodiment of the present invention.

FIG. 2 is a view illustrating a configuration of the pouch 3 in accordance with an embodiment of the present invention. As shown in FIG. 2, the pouch 3 includes a storage bag 31 having an insertion hole 32, a face plate 33, and a pocket 34. The storage bag 31 is a bag in which stool and/or a gaseous matter discharged from the stoma 21 can be stored. The insertion hole 32 is a hole into which the stoma 21 is to be inserted when the pouch 3 is attached to the user 2. The face plate 33 is disposed to surround the insertion hole 32 in form of a circle. The face plate 33 has a surface having an adhesive applied thereto. In attachment of the pouch 3, the user 2 inserts the stoma 21 into the insertion hole 32 and firmly presses the face plate 33 onto a skin of the abdominal region of the user 2. With this, the face plate 33 is fixed to the skin of the user 2 via the adhesive so as to surround the stoma 21. As a result, the skin surrounding the stoma 21 is sealed by the face plate 33.

The pocket 34 is formed at a portion of the storage bag 31 which portion is under the face plate 33. As will be described in detail later, the pocket 34 functions as an attachment section via which the sensor device 4 is attached to the pouch 3.

(Configuration of Sensor Device 4)

Figure 3:
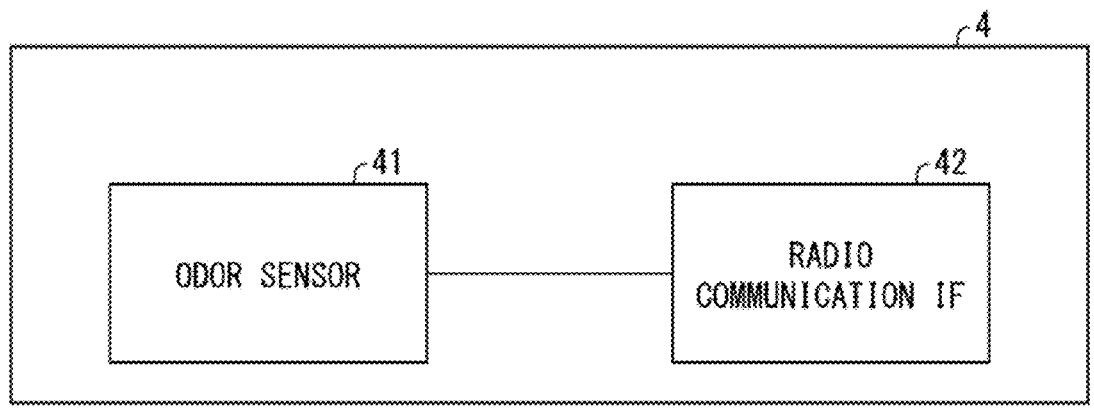
FIG. 3 is a block diagram illustrating a configuration of a sensor device in accordance with an embodiment of the present invention.

FIG. 3 is a block diagram illustrating a configuration of the sensor device 4 in accordance with an embodiment of the present invention. As shown in FIG. 3, the sensor device 4 includes an odor sensor 41 and a radio communication interface 42 (transmitting section, notification section). The odor sensor 41 detects odor leaking from the pouch 3 attached to the stoma 21 of the user 2. To be more specific, the odor sensor 41 is disposed close to the pouch 3, and detects odor (gas) leaking from the pouch 3 through a gap between the face plate 33 of the pouch 3 and the skin of the user 2 when such a gap is generated. Upon detection of odor, the odor sensor 41 outputs a detection signal to the radio communication interface 42.

The radio communication interface 42 is a communication interface used to perform radio communication with the notification device 5. In this embodiment, the radio communication interface 42 is a Bluetooth (registered trademark) interface, for example. In this case, the radio communication interface 42 transmits, to the notification device 5 over Bluetooth communication, a detection signal supplied from the odor sensor 41.

(Configuration of Notification Device 5)

Figure 4:
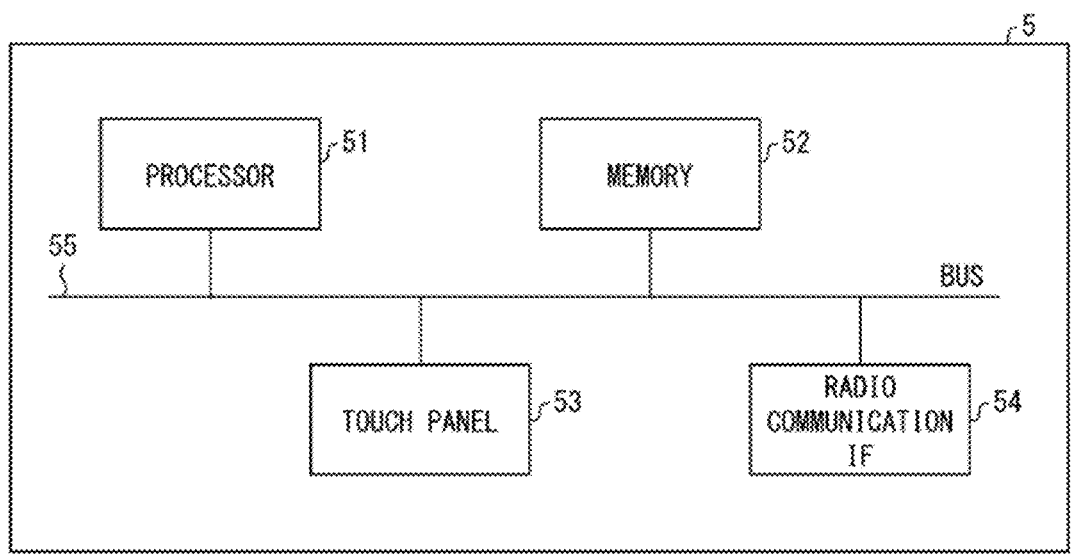
FIG. 4 is a block diagram illustrating a configuration of a notification device in accordance with an embodiment of the present invention.

FIG. 4 is a block diagram illustrating a configuration of the notification device 5 in accordance with an embodiment of the present invention. As shown in FIG. 4, the notification device 5 includes a processor 51, a memory 52, a touch panel 53, a radio communication interface 54 (receiving section), and a bus 55. The processor 51, the memory 52, the touch panel 53, and the radio communication interface 54 are connected to each other via the bus 55. A device usable as the notification device 5 may be, for example, any of various portable terminal devices such as a smartphone or a tablet personal computer (PC).

The memory 52 stores a notification program therein. The processor 51 executes various processes included in the later-described notification method, in accordance with a command included in the notification program stored in the memory 52. The processor 51 is a central processing unit (CPU), for example. The memory 52 is a flash memory, for example. The touch panel 53 is a panel in which a display panel functioning as an output device and a touch panel functioning as an input device are integrated together. As will be described in detail later, the notification device 5 displays, on the touch panel 53, a message for notifying the user 2 of odor leakage from the pouch 3. That is, the notification device 5 is one example of the notification device used to notify the user 2 of odor leakage.

The radio communication interface 54 is an interface used to perform radio communication with another device. The radio communication interface 54 can include an interface used to perform radio communication with another device not via a network, for example, a Bluetooth (registered trademark) interface. The radio communication interface 54 can include an interface used to perform radio communication with another device via a local area network (LAN), for example, a Wi-Fi (registered trademark) interface. The radio communication interface 54 can include an interface used to perform radio communication with another device via a mobile communication network, for example, a 5G interface. In this embodiment, the radio communication interface 54 used to perform communication with the sensor device 4 employs a Bluetooth interface.

(Arrangement Example of Sensor Device 4)

Figure 5:
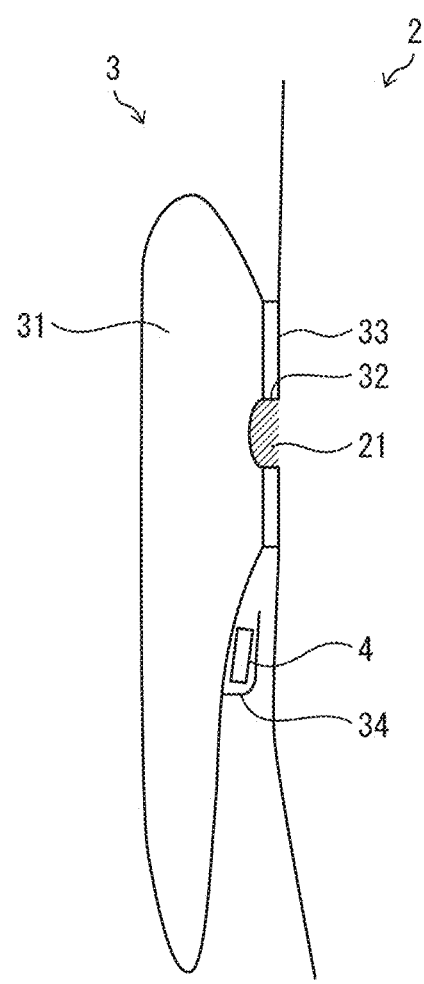
FIG. 5 is a view illustrating the pouch with the sensor device stored in a pocket of the pouch.

FIG. 5 is a view illustrating the pouch 3 with the sensor device 4 stored in the pocket 34. In FIG. 5, the pouch 3 attached to the stoma 21 of the user 2 is viewed from a lateral side of the body of the user 2. A right side part of FIG. 5 corresponds to the abdominal region of the user 2. As shown in FIG. 5, the pouch 3 is attached to the user 2 in a state where the stoma 21 is inserted into the insertion hole 32 and the face plate 33 is in close contact with the skin of the abdominal region of the user 2. In the pocket 34 formed under the face plate 33, the sensor device 4 is stored. The user 2 can then attach the pouch 3 to him/her after putting the sensor device 4 into the pocket 34. In this manner, the user 2 can dispose the sensor device 4 at a position under the face plate 33. Alternatively, the user 2 may put the sensor device 4 into the pocket 34 after attaching the pouch 3 to him/her.

(One Example of Notification Method)

Figure 6:
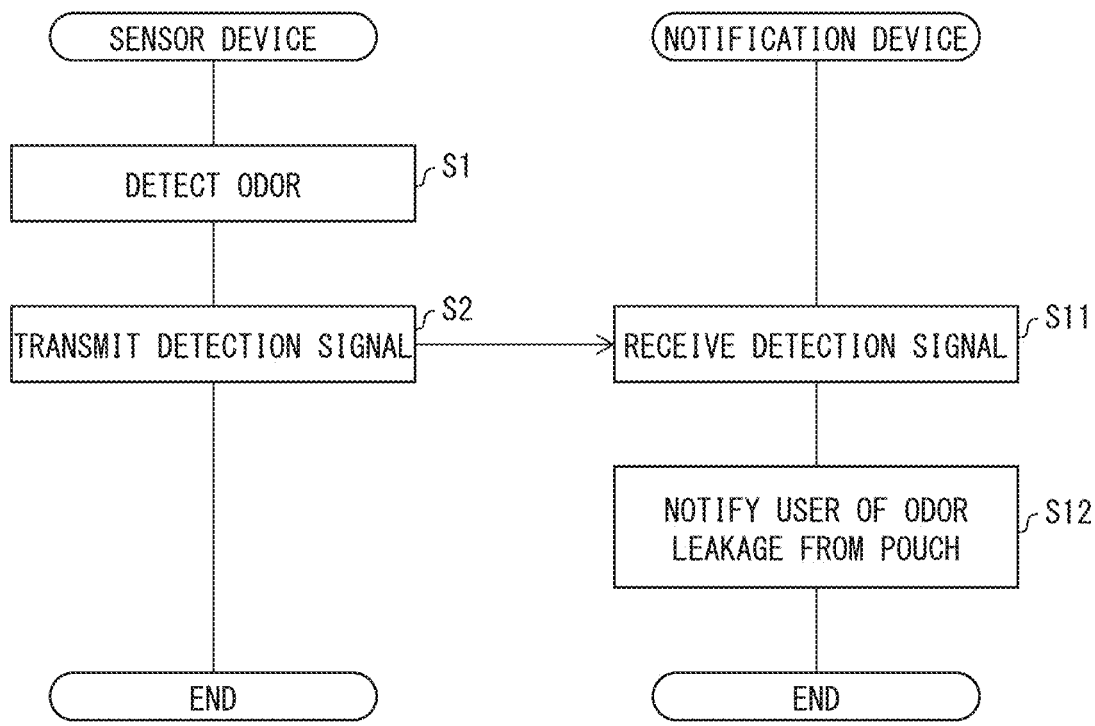
FIG. 6 is a sequence diagram illustrating a flow of a notification method to be executed by a notification system in accordance with an embodiment of the present invention.

FIG. 6 is a sequence diagram illustrating a flow of a notification method to be executed by the notification system 1 in accordance with an embodiment of the present invention. The user 2 wears the pouch 3 attached thereto, with the sensor device 4 stored in the pocket 34. The user 2 further possesses the notification device 5. Bluetooth pairing between the sensor device 4 and the notification device 5 is established in advance. In each of the sensor device 4 and the notification device 5, Bluetooth function is turned on.

Assume that, in this situation, odor leaks from the pouch 3 as a result of generation of a gap between the face plate 33 and the skin of the user 2 for some reasons. The notification system 1 executes the notification method shown in FIG. 6 to detect the odor leakage and notify the user 2 of the odor leakage. In step S1, first, the odor sensor 41 in the sensor device 4 detects odor leaking from the gap between the face plate 33 and the skin of the user 2. If the sensor device 4 detects odor, the sensor device 4 outputs a detection signal to the radio communication interface 42. In step S2, the radio communication interface 42 of the sensor device 4 transmits the detection signal to the notification device 5 via Bluetooth communication. In step S11, the radio communication interface 54 of the notification device 5 receives the detection signal transmitted from the sensor device 4. The radio communication interface 54 notifies the processor 51 that the detection signal is received. In step S12, the processor 51 notifies the user 2 that the odor leakage from the pouch 3 is detected.

As shown in FIG. 6, as a result of the radio communication interface 42 transmitting the detection signal to the notification device 5, the user 2 is notified that the odor leakage from the pouch 3 is detected. From this perspective, it can be said that the radio communication interface 42 functions as a notification section that notifies, via the notification device 5, the user 2 that odor leakage from the pouch 3 is detected.

The above description has dealt with the configuration in which the sensor device 4 determines the presence or absence of odor leakage from the pouch 3. However, the present invention is not limited to this. Alternatively, for example, the notification device 5 may determine the presence or absence of odor leakage from the pouch 3. In this case, the detection signal transmitted from the sensor device 4 to the notification device 5 is an output signal from the odor sensor 41, rather than a detection signal that is generated in accordance with the output signal from the odor sensor 41 and that indicates the presence or absence of odor leakage. The notification device 5 determines the presence or absence of odor leakage in accordance with the output signal from the odor sensor 41. Then, if odor leakage is present, the notification device 5 notifies the user 2 of the presence of odor leakage.

(One Example of Notification Message)

Figure 7:
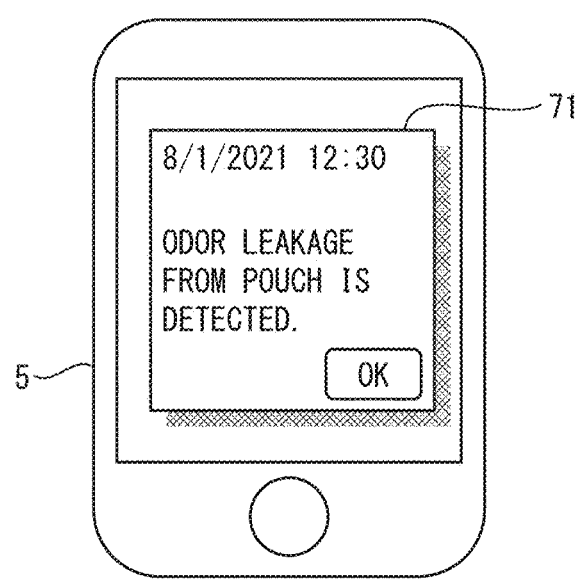
FIG. 7 is a view illustrating an example of a message that notifies a user that odor leaking from the pouch is detected.

FIG. 7 is a view illustrating an example of a message that notifies the user 2 that odor leaking from the pouch 3 is detected. The processor 51 displays a message 71 such as the one shown in FIG. 7 on the touch panel 53, so as to notify the user 2 that odor leaking from the pouch 3 is detected. The message 71 includes a text stating that odor leaking from the pouch 3 is detected. The user 2 visually recognizes the message 71, and knows occurrence of odor leakage from the pouch 3. In response to this, the user 2 takes a measure to remove the problem of odor leakage.

(Major Effects)

The notification system 1 in accordance with the present embodiment notifies the user 2 of odor leakage in a case where odor leakage from the pouch 3 attached to the user 2 is detected. With this, even in a case where a very small amount of odor leaks from a small gap between the face plate 33 and the skin of the user 2, it is possible to detect the leakage from the pouch. Therefore, it is possible to detect leakage from the pouch 3 with a higher accuracy.

Furthermore, at a stage in which a content (stool) of the pouch 3 does not leak from the pouch yet, the notification system 1 can notify the user 2 of odor leakage to allow the user 2 to take a measure to deal with the odor leakage. With this, the user 2 does not have to remove the content having leaked from the pouch 3 or to wash his/her skin to which the content is adhered. This can significantly save the labor required to deal with the leakage.

(Preferred Arrangement of Sensor Device 4)

The sensor device 4 is preferably disposed as close to an outer peripheral surface of the face plate 33 as possible. For example, the sensor device 4 may be disposed at any position in an area surrounding the face plate 33. With this, it is possible to reduce a distance from (i) a gap between the face plate 33 and the skin of the user 2 to (ii) the odor sensor 41, thereby making it possible to expose odor leaking from the gap to the odor sensor 41 in a short time. This makes it possible to expose, to the odor sensor 41, gas having a higher concentration, thereby further increasing the accuracy in detection of odor. Particularly, the sensor device 4 is preferably disposed at a distance within 10 cm from the outer peripheral surface of the face plate 33. This can prevent a phenomenon that the odor sensor 41 senses odor in a surrounding area which odor is not odor of gas having leaked from the pouch 3, thereby suppressing or reducing erroneous detection of leakage.

(Hook 81)

Figure 8:
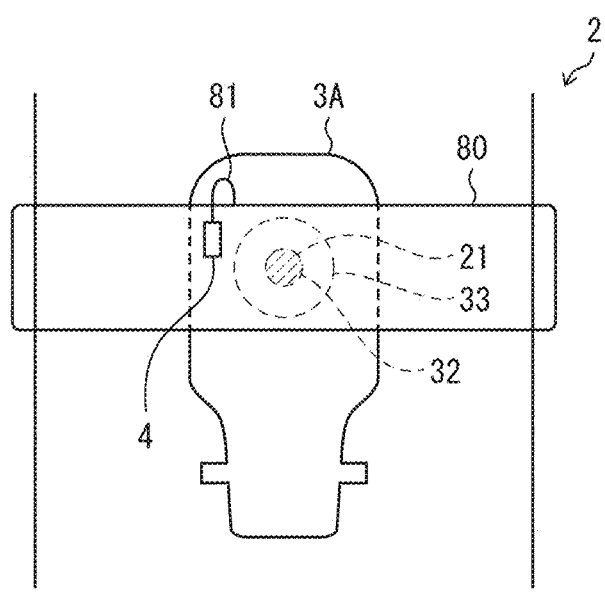
FIG. 8 is a view illustrating a pouch fixed by a belt with a sensor device attached to a hook of the belt.

FIG. 8 is a view illustrating a pouch 3A fixed by a belt 80 with the sensor device 4 attached to a hook 81 of the belt 80. In the example shown in FIG. 8, the user 2 wears the pouch 3A attached to him/her. The pouch 3A includes a storage bag 31 having an insertion hole 32 and a face plate 33, but does not include a pocket 34. Thus, the user 2 cannot attach the sensor device 4 to the pouch 3A.

The user 2 further wears the belt 80 to fix the pouch 3A to the abdominal region of the user 2. The belt 80 is wound around the abdominal region of the user so as to cover the pouch 3A. The belt 80 is provided with the hook 81. Via the hook 81, the sensor device 4 is hooked on the belt 80, whereby the sensor device 4 is attached. When the user wears the belt 80, the hook 81 is disposed close to the face plate 33. Thus, when the user 2 attaches the sensor device 4 to the hook 81 of the belt 80, the sensor device 4 is also disposed close to the face plate 33.

In the example of FIG. 8, the sensor device 4 can be disposed close to the face plate 33 of the pouch 3A, which does not include the pocket 34. Thus, even the user 2 who uses the conventional, generally-used pouch 3A can utilize the notification system 1. Note that, even in a case where the user 2 uses the pouch 3 including the pocket 34, the user 2 may further wear the belt 80 provided with the hook 81 and hook the sensor device 4 on the belt 80 via the hook 81. Instead of the configuration in which the sensor device 4 is hooked on the hook 81 fixed to the belt 80, a hook 81 fixed to the sensor device 4 may be hooked on the belt 80.

(Sensor Device 4A)

Figure 9:
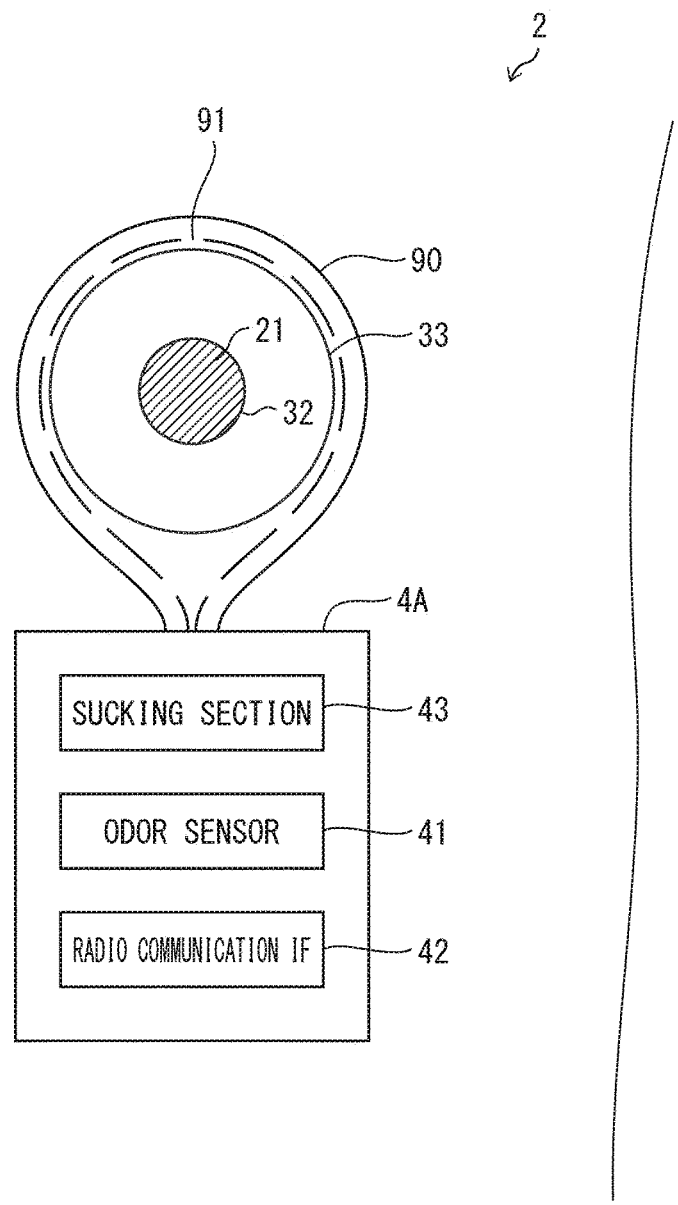
FIG. 9 is a view illustrating a configuration of a sensor device including a sucking section.

FIG. 9 is a view illustrating a configuration of a sensor device 4A including a sucking section 43. In the example shown in FIG. 9, the user 2 wears the pouch 3A attached to him/her. For convenience of explanation, FIG. 9 does not illustrate the storage bag 31. The user 2 uses a hose 90 to attach the sensor device 4A to the pouch 3A. The sensor device 4A includes an odor sensor 41, a radio communication interface 42, and a sucking section 43. The sucking section 43 is a mechanism for sucking gas. The sucking section 43 exposes sucked gas to the odor sensor 41.

The hose 90 is a tube that is hollow on its inside and that has a side surface including a plurality of sucking holes 91. The hose 90 has two opposite ends both connected to the sucking section 43 of the sensor device 4A. The hose 90 is hooked on the outer periphery of the face plate 33, and the sensor device 4A connected to the hose 90 is attached at a location under the face plate 33.

The sucking section 43 of the sensor device 4A sucks the inside of the hose 90, so as to suck gas in an area surrounding the face plate 33 through the sucking holes 91 of the hose 90. If the sucked gas contains a certain concentration or more of gaseous matter leaking from the pouch 3, the odor sensor 41 detects odor leakage from the pouch 3.

In this example, the sucking section 43 uses the hose 90 to suck gas. This can give directivity to a sucking direction of gas. Thus, it is possible to effectively suck a gaseous matter leaking from the face plate 33. Consequently, it is possible to further increase the accuracy in detection of odor leakage from the pouch.

The hose 90 also functions as a hook via which the sensor device 4A is attached to the pouch 3A. This can eliminate the need for an additional part used to attach the sensor device 4A, such as a hook.

(Attachment of Sensor Device 4 Via Hook-and-Loop Fastener 101)

Figure 10:
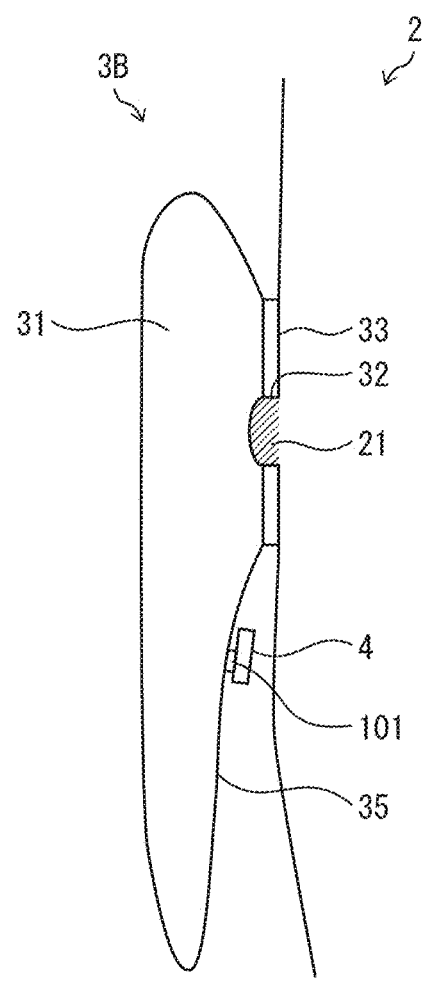
FIG. 10 is a view illustrating a pouch to which a sensor device is attached via a hook-and-loop fastener.

FIG. 10 is a view illustrating a pouch 3B to which the sensor device 4 is attached via a hook-and-loop fastener 101. In FIG. 10, the pouch 3B attached to the stoma 21 of the user 2 is viewed from a lateral side of the body of the user 2. A right side part of FIG. 10 corresponds to the abdominal region of the user 2. The pouch 3B shown in FIG. 10 is substantially identical in configuration to the above-described pouch 3. However, the pouch 3B differs from the pouch 3 in the following point. That is, the pouch 3B includes a storage bag 31 having a back surface 35 that comes into contact with the skin of the user 2 when the pouch 3B is attached to the user 2 and that is made of a nonwoven fabric. Since the back surface 35 of the pouch 3B is made of a nonwoven fabric, which favorably agrees with the skin of the user 2, it is possible to reduce a sense of discomfort that may occur in the skin of the user 2 while the user 2 is attaching the pouch 3B to him/her.

In the example shown in FIG. 10, the sensor device 4 is attached, via the hook-and-loop fastener 101, to a portion of the back surface 35 of the pouch 3B which portion is under the face plate 33. That is, the hook-and-loop fastener 101 functions as an attachment section via which the sensor device 4 is attached to the pouch 3B. The user 2 can apply the hook-and-loop fastener 101 onto a housing of the sensor device 4 and firmly press, onto the back surface 35 of the pouch 3B, an attachment surface of the hook-and-loop fastener 101 on the sensor device 4. With this, the user 2 can attach the sensor device 4 to the back surface 35 of the pouch 3B.

In the example shown in FIG. 10, the sensor device 4 can be disposed close to the face plate 33 of the pouch 3B not including the pocket 34. Thus, even the user 2 who uses the conventional, generally-used pouch 3B can utilize the notification system 1.

Alternatively, the user 2 can attach the sensor device 4 to the back surface 35 of the pouch 3B, without directly applying the hook-and-loop fastener 101 to the sensor device 4. Specifically, the user 2 applies the hook-and-loop fastener 101 to a surface of a nonwoven fabric bag (not illustrated) made of a nonwoven fabric, and then stores the sensor device 4 in the nonwoven fabric bag. Thereafter, the user 2 firmly presses, onto the back surface 35 of the pouch 3B, the attachment surface of the hook-and-loop fastener 101 on the nonwoven fabric bag in which the sensor device 4 is stored, thereby attaching the nonwoven fabric bag to the back surface 35 of the pouch 3B. Consequently, the user 2 can attach the sensor device 4 stored in the nonwoven fabric bag to the back surface 35 of the pouch 3B.

In this example, since the sensor device 4 is stored in the nonwoven fabric bag, the sensor device 4 would not come into direct contact with the skin of the user 2. Thus, it is possible to eliminate a sense of discomfort that can occur as a result of contact of the sensor device 4 with the skin. Furthermore, since the sensor device 4 is stored in the nonwoven fabric bag, the skin of the user 2 comes into contact with the nonwoven fabric bag. The nonwoven fabric bag is made of a nonwoven fabric, which favorably agrees with the skin of the user 2. Thus, it is possible to reduce a sense of discomfort that may occur in the skin of the user 2 while the user 2 uses the sensor device 4.

(Notification Mode)

The notification of odor leakage to the user 2 is not limited to notification appealing to a visual sense of the user 2, such as the one shown in FIG. 7. Alternatively, the notification may be the one appealing another sense (e.g., auditory sense, tactile sense) other than the visual sense. For example, the processor 51 may cause the notification device 5 to vibrate in a given vibration pattern so as to notify the user 2 of odor leakage from the pouch 3. In this example, even while the user 2 has the notification device 5 stored in a bag or a pocket of his/her clothing, the user 2 can quickly know occurrence of odor leakage from the pouch 3. This can avoid a situation in which the user 2 misses the notification and is late to take a measure to remove the problem of odor leakage.

The notification of odor leakage to the user 2 is preferably performed in a mode in which the notification is not noticed by people around the user 2, specifically, in a mode in which the notification appeals to the visual or tactile sense of the user 2. If the notification is carried out by display of the message 71 or vibrations of the notification device 5, the occurrence of odor leakage from the pouch 3 is not noticed by the people around the user 2. This can protect privacy of the user. Furthermore, this allows the user 2 to go a lavatory to take a measure to remove the problem of odor leakage without having to mind the people around the user.

(Detection of Leakage of Content)

In a case where the user 2 is sleeping, resting, or the like and the user 2 takes a certain posture such as a supine position or a side-laying position, a content such as solid stool or aqueous stool stored in the pouch 3 can leak from the pouch 3 before a gaseous matter leaks. Even in such a case, the sensor device 4 can detect, by the odor sensor 41, odor emitted from the leaked content to detect occurrence of leakage of the content from the pouch 3. Thus, even in a case where the content leaks from the pouch 3A before a gaseous matter leaks, the notification system 1 can notify the user 2 that the leakage is detected.

(Attachment Training)

The notification system 1 can be utilized for training of attachment of the pouch 3, targeted to a user 2 who is unused to attachment of the pouch 3. Specifically, the user 2 first attaches, to him/her, the pouch 3 having the pocket 34 in which the sensor device 4 is stored. Then, the user 2 possesses the notification device 5 and spends time until a predetermined period of time elapses. If the user 2 can spend a certain period of time without receiving a notification of odor leakage from the notification device 5, the user 2 acknowledges that he/she could attach the pouch 3 properly.

Meanwhile, if the user 2 receives a notification of odor leakage from the notification device 5 before the certain period of time elapses, the user 2 acknowledges that he/she could not attach the pouch 3 properly. In this case, the user 2 attaches the pouch 3 from the start over again. In this manner, the user 2 repeatedly performs attachment of the pouch 3 until the user 2 can spend the certain period of time without receiving a notification of odor leakage from the notification device 5 after the attachment of the pouch 3. By taking this attachment training, the user 2 can learn, in a short time, how to attach the pouch 3.

(Use of Cloud Server)

The notification device 5 may transmit, to the cloud server, detection information indicating detection of odor leakage, in a case where a detection signal from the sensor device 4 is received. For example, time information indicating time when the odor leakage was detected is transmitted to the cloud server. The cloud server adds the received time information to a history of the detection information indicating detection of odor leakage. The cloud server analyzes the history to predict time having a high possibility that next odor leakage may occur in the pouch 3 attached to the user 2, and transmits time information indicating the time to the notification device 5. The notification device 5 notifies the user 2 of the time indicated by the notified time information, so as to make the user 2 know in advance a timing at which next odor leakage from the pouch 3 is likely to occur. With this, the user 2 can take a preventive measure against odor leakage when the time approaches. Thus, the user 2 can perform daily activities at more ease.

SUPPLEMENTARY REMARKS

The present invention is not limited to the above embodiments, but can be altered by a person skilled in the art within the scope of the claims. The present invention also encompasses, in its technical scope, any embodiment derived by combining technical means disclosed in differing embodiments described above.

REFERENCE SIGNS LIST

1: notification system
2: user
3, 3A, 3B: pouch
4, 4A: sensor device
5: notification device
15: bus
21: stoma
31: storage bag
32: insertion hole
33: face plate
34: pocket
35: back surface
41: sensor
42, 54: radio communication interface
43: sucking section
51: processor
52: memory
53: touch panel
71: message
80: belt
81: hook
90: hose
91: sucking hole
101: hook-and-loop fastener

The invention claimed is:

1. A sensor device comprising:
an odor sensor that detects odor leaking from a pouch attached to a stoma of a user;
a notification section that notifies the user that the odor is detected; and
a sucking section that sucks gas in an area surrounding a face plate of the pouch, wherein
a belt designed to fix the pouch to the user is wound around the user so as to cover the pouch,
the belt is provided with a hook which is disposed close to the face plate of the pouch while the belt is wound around the user,
the sensor device is attached to an outer side of the pouch and attached to the hook of the belt so as to be disposed close to the face plate of the pouch, and
if the gas sucked by the sucking section contains a certain concentration or more of gaseous matter leaking from the pouch, the odor sensor detects odor leakage from the pouch.

2. The sensor device as set forth in claim 1, wherein the sensor device is stored in a pocket formed in a storage bag of the pouch.

3. A pouch that is to be attached to a stoma of a user, comprising:
an attachment section via which the sensor device recited in claim 1 is attached to the pouch.

4. The sensor device as set forth in claim 1, wherein the sucking section sucks the gas through sucking holes on a side surface of a hole having two opposite ends both connected to the sucking section.

5. A notification method comprising the steps of:
detecting odor leaking from a pouch attached to a stoma of a user by using a sensor device attached to an outer side of the pouch; and
notifying the user that the odor is detected, wherein
a belt designed to fix the pouch to the user is wound around the user so as to cover the pouch,
the belt is provided with a hook which is disposed close to a face plate of the pouch while the belt is wound around the user,
the sensor device is attached to the hook of the belt so as to be disposed close to the face plate of the pouch, and
in the step of detecting, if the gas which is sucked by a sucking section of the sensor device and which is in an area surrounding the face plate contains a certain concentration or more of gaseous matter leaking from the pouch, odor leakage from the pouch is detected.

6. A notification system comprising:
a sensor device; and
a notification device,
the sensor device including
an odor sensor that detects odor leaking from a pouch attached to a stoma of a user,
a transmitting section that transmits, to the notification device, a detection signal obtained by the odor sensor, and
a sucking section that sucks gas in an area surrounding a face plate of the pouch, wherein
a belt designed to fix the pouch to the user is wound around the user so as to cover the pouch,
the belt is provided with a hook which is disposed close to a face plate of the pouch while the belt is wound around the user, the sensor device is attached to an outer side of the pouch and attached to the hook of the belt so as to be disposed close to the face plate of the pouch, and if the gas sucked by the sucking section contains a certain concentration or more of gaseous matter leaking from the pouch, the odor sensor detects odor leakage from the pouch, the notification device including
   a receiving section that receives the detection signal and
   a notification section that notifies the user that the odor is detected, in a case where the detection signal is received.

\* \* \* \* \*